US011206246B2

(12) United States Patent
Krishnamacharya

(10) Patent No.: US 11,206,246 B2
(45) Date of Patent: Dec. 21, 2021

(54) CONTROLLING ACCESS TO SECURED DATA IN MULTI-SYSTEM EXCHANGE ENVIRONMENTS

(71) Applicant: EQUIFAX INC., Atlanta, GA (US)

(72) Inventor: Sri Krishnamacharya, Cumming, GA (US)

(73) Assignee: EQUIFAX INC., Atlanta, GA (US)

( * ) Notice: Subject to any disclaimer, the term of this patent is extended or adjusted under 35 U.S.C. 154(b) by 142 days.

(21) Appl. No.: 16/680,794

(22) Filed: Nov. 12, 2019

(65) Prior Publication Data

US 2021/0144131 A1     May 13, 2021

(51) Int. Cl.
*H04L 29/06*     (2006.01)
*H04L 9/08*     (2006.01)
*H04L 9/32*     (2006.01)

(52) U.S. Cl.
CPC ........ *H04L 63/0471* (2013.01); *H04L 9/0819* (2013.01); *H04L 9/3234* (2013.01); *H04L 63/18* (2013.01)

(58) Field of Classification Search
CPC ............. H04L 63/0471; H04L 63/0428; H04L 63/0464; H04L 9/0894; H04L 9/0819; H04L 9/3234; H04L 63/18; H04L 2209/60; G06F 21/602; G06F 21/6245
See application file for complete search history.

(56) References Cited

U.S. PATENT DOCUMENTS

| | | | | |
|---|---|---|---|---|
| 7,181,017 | B1* | 2/2007 | Nagel | H04L 9/0825 380/282 |
| 2011/0313928 | A1* | 12/2011 | Blonchek | G16H 10/60 705/51 |
| 2014/0351924 | A1* | 11/2014 | Myers | H04L 63/0435 726/15 |

FOREIGN PATENT DOCUMENTS

EP      3014516 A1     5/2016

OTHER PUBLICATIONS

PCT/US2020/060237, "International Search Report and Written Opinion", dated Feb. 26, 2021, 15 pages.

\* cited by examiner

*Primary Examiner* — Yogesh Paliwal
(74) *Attorney, Agent, or Firm* — Kilpatrick Townsend & Stockton LLP

(57) ABSTRACT

An exchange processing system may include multiple exchange components that are respectively included in multiple computing systems. A central exchange component may receive a request to enable access to secured data, the request having identity data encrypted via an identity encryption module and inquiry data encrypted via a first request encryption module. The central exchange component may decrypt the identity data via the identity encryption module, and decrypt the inquiry data via the first request encryption module. Response data may be generated from secured data that is selected based on the identity and inquiry data. The central exchange component may encrypt the response data via a second request encryption module and re-encrypt the identity data via the identity encryption module. The encrypted identity and response data may be provided to a second remote exchange module.

11 Claims, 7 Drawing Sheets

CONTROLLING ACCESS TO SECURED DATA IN MULTI-SYSTEM EXCHANGE ENVIRONMENTS

TECHNICAL FIELD

This disclosure relates generally to the field of data security, and more specifically relates to securing data at multiple computing systems.

BACKGROUND

Information processing systems may create and store secured data for a person. The secured data may represent sensitive personal or protected information, such as employment history, educational information, financial information, or medical history. Other information processing systems may request access to the secured data, such as to fulfill a request of the person or to comply with another obligation. To fulfill the request, a conventional information processing system may select and encrypt data, and transmit the encrypted data across a computing network. However, transmission of sensitive information across a computing network may expose the information to risk, such as tampering or theft of the sensitive information. Although a conventional information processing system responding to a data request may encrypt data prior to transmission across a network, encrypted data may still be decrypted or otherwise compromised by a malicious actor.

SUMMARY

According to certain aspects, an exchange processing system may include multiple exchange components that are respectively included in multiple computing systems. A central exchange component may receive, from a first remote exchange component, a request to enable access to secured data. The request may include identity data that is encrypted by the first remote component via a first portion of an identity encryption module, and inquiry data that is encrypted by the first remote component via a first portion of a first request encryption module. The central exchange component may decrypt the identity data via a second portion of the identity encryption module, and decrypt the inquiry data via a second portion of the first request encryption module.

The central exchange component may receive response data. The response data may be generated a selected portion of the secured data. In addition, the selected portion of the secured data may be accessed based on the decrypted identity data and the decrypted inquiry data. The central exchange component may encrypt the response data via a first portion of a second request encryption module, and re-encrypt the identity data via the second portion of the identity encryption module. The central exchange component may provide the encrypted response data and re-encrypted identity data to a second remote exchange component. The second remote exchange component may be configured to decrypt the encrypted response data via a second portion of the second request encryption module and to decrypt the re-encrypted identity data via a third portion of the identity encryption module.

In an additional or alternative aspect, a remote exchange component may receive, from a central exchange component, a request to access secured data. The secured data may be accessible via a data access module. The remote exchange component may provide the request to the data access module. The remote exchange component may receive the secured data from the data access module. Responsive to receiving the secured data, the remote exchange component may generate transformed data that represents the secured data. The remote exchange component may provide the transformed data to the central exchange component.

These illustrative aspects are mentioned not to limit or define the disclosure, but to provide examples to aid understanding thereof. Additional aspects are discussed in the Detailed Description, and further description is provided there.

BRIEF DESCRIPTION OF THE DRAWINGS

Features, aspects, and advantages of the present disclosure are better understood when the following Detailed Description is read with reference to the accompanying drawings, where.

DETAILED DESCRIPTION

Figure 1:
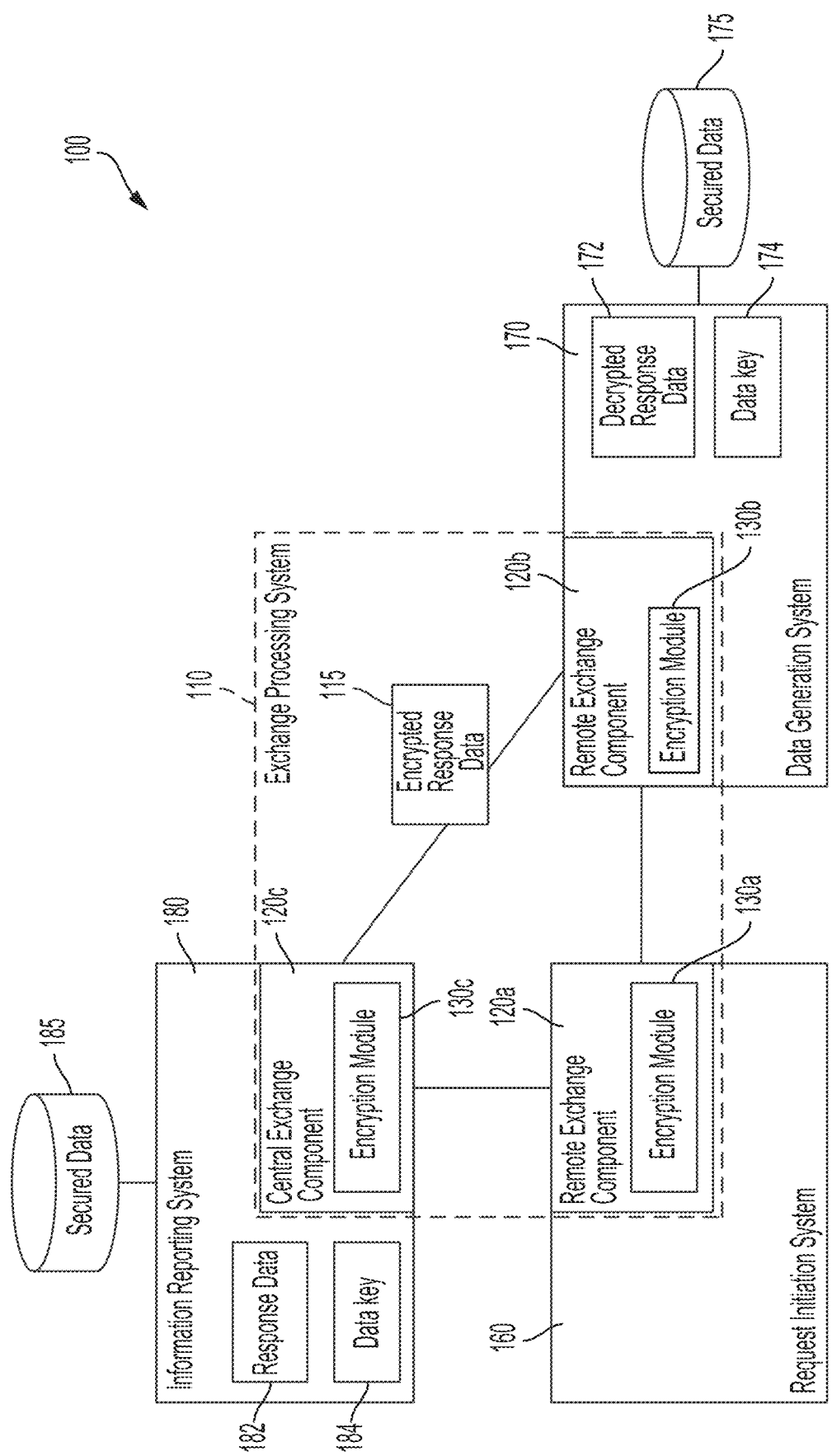
FIG. 1 is a block diagram depicting an example of a computing environment in which access is controlled for secured data stored by multiple computing systems, according to certain aspects.

As discussed above, contemporary information processing systems that transmit secured data in response to a data request may not adequately protect sensitive information represented by the transmitted data. Certain aspects described herein can address this deficiency with respect to sensitive data transmission over data networks. For example, a server system can control access to secured data by reducing network-accessible storage locations of secured data, and by avoiding transmission of secured data between computing systems.

The following examples are provided to introduce certain aspects of the present disclosure. A person who is performing a transaction with an organization may wish to request access to his or her sensitive information on behalf of the organization. The sensitive data may include personally identifiable information ("PII"), or other types of sensitive or personal data. In addition, the sensitive data may be generated by multiple computing systems, such as computing systems that are under operation of respective organizations. Computing systems that are under the operation of these entities (e.g., a requesting person, organizations that generate sensitive data) can request access to sensitive information via an exchange processing system. The exchange processing system can be a server system having processing hardware for executing a central exchange component. The exchange processing system can also include multiple remote exchange components that are software modules configured to be executed by additional processing hardware of an additional computing system. The central exchange component can be included in an information reporting system, and the multiple remote exchange components can each be included in respective additional computing systems. The exchange processing system may be configured such that the central exchange component is capable of communicating with each remote exchange component via a secure communication channel. In addition, the central exchange component may include one or more instances of various encryptions modules. A first encryption module may have a first instance on the central exchange component and a second instance on a remote exchange component, such that the central and remote exchange components are capable of encrypting and decrypting data via the instances of the first encryption module. A second encryption module may have a first instance on the central exchange component and a second instance on an additional remote exchange component, such that the central and additional remote exchange components are capable of encrypting and decrypting data via the instances of the second encryption module.

Continuing with this example, the exchange processing system can control access to secured data in the computing systems in which the multiple exchange components are included. For instance, a requesting system, such as a computing system of a person who wishes to request his or her personal data, provides an access request to a first remote exchange component included in the person's computing system. The access request indicates a request for secured data and a recipient of the requested secured data. The recipient may be an additional computing system of an organization designated by the person. The first remote exchange component encrypts the access request via a first instance of a first encryption module and provides the encrypted request to the central exchange component that is included in an information reporting system. The central exchange component decrypts the request via a second instance of the first encryption module. In addition, the central exchange component provides the decrypted request to an information reporting system that is capable of accessing the requested secured data.

Responsive to receiving the decrypted request, the information reporting system generates response data for the access request and provides the response data to the central exchange component. The central exchange component encrypts the response data via a first instance of a second encryption module and transmits the encrypted response data to a second remote exchange component included in a data generation system that is indicated as the recipient, such as the additional computing system of the organization designated by the person. Responsive to receiving the encrypted response data, the second remote exchange component decrypts the encrypted response data via a second instance of the second encryption module, and provides the decrypted response data to the data generation system. In this example, the access request and the response data are encrypted and/or transformed upon receipt by the exchange processing system. Security of the secured data may be improved by the encryption or transformation, such as by limiting storage of the secured data on a network-accessible location, e.g., the exchange components.

In some aspects, the unconventional arrangement of the exchange components on multiple computing systems may provide a technical advantage to controlling access to secured data. In particular, the interaction of the exchange components can offer an improvement to the computer-centered problem of controlling access to secured data that is stored by multiple computing systems. For example, the instances of the multiple encryption modules may provide a technical advantage by enabling only an exchange component having an instance of a particular encryption module to encrypt or decrypt data that is handled by the particular encryption module. In addition, the exchange component may encrypt or decrypt data based on a particular data key received from the component's computing system. This technique of tying the functions of a particular exchange component to a particular computing system may offer an unexpected way to improve security, by increasing the difficulty for a malicious actor to misuse the particular exchange component.

Referring now to the drawings, FIG. 1 is a block diagram depicting an example of a computing environment 100 in which access is controlled for secured data stored by multiple computing systems. The multiple computing systems may include computing systems that are different from each other, such as separate systems that are capable of communicating via a computing network. In addition, the multiple computing systems may include computing systems that are under operational control by multiple distinct entities (e.g., end-users, business organizations, governmental agencies). Each of the multiple computing systems may include one or more physical computing devices (e.g., smartphone, server) or virtual computing devices (e.g., virtual device, cloud computing).

In FIG. 1, the computing environment 100 includes a request initiation system 160, a data generation system 170, and an information reporting system 180. Each of the systems 160, 170, and 180 can communicate via one or more computing networks. In addition, each of the systems 160, 170, and 180 can communicate via an exchange processing system 110. The exchange processing system 110 may include multiple exchange components that are included in respective computing systems of the environment 100. For example, the exchange processing system 110 may include a central exchange component 120c, a remote exchange component 120a, and a remote exchange component 120b. The central exchange component 120c may be installed on (or otherwise operate within) the information reporting system 180, the remote exchange component 120a may be installed on the request initiation system 160, and the remote exchange component 120b may be installed on the data generation system 170. Each exchange component includes program code that is executable by one or more processing devices of the respective computing system in which the exchange component is included. In some cases, a remote exchange component of the exchange processing system 110 that is included in a particular computing system can interact with the particular computing system without receiving operational control information from the particular computing system. For example, the remote exchange component 120a can interact with the request initiation system 160 via software communications (e.g., API calls) that are passed between the remote exchange component 120a and the system 160, and may be further configured to receive operational control information (e.g., updates) via the central exchange component 120c.

Each exchange component in the exchange processing system 110 can communicate with at least one other exchange component in the exchange processing system 110 via a secure communication channel. In addition, the central exchange component 120c can communicate with each additional exchange component in the exchange processing system 110. For instance, the central exchange component 120c and the remote exchange component 120a can communicate via a first secure channel, and the central exchange component 120c and the remote exchange component 120b can communicate via a second secure channel. In addition, the remote exchange component 120a and the remote exchange component 120b can communicate via a third secure channel. In FIG. 1, the remote exchange components 120a and 120b are configured as sharing a secure communication channel, but other implementations are possible, such as a remote exchange component that is configured to communicate with the central exchange component 120c but not with an additional remote exchange component.

In addition, each particular exchange component in the exchange processing system 110 may include one or more encryption modules that are configured to encrypt and/or decrypt transmissions that are received or provided by the particular exchange component. Each encryption module (or instance of an encryption module) includes program code that is executable by one or more processing devices of the respective computing system in which the particular exchange component is included. In FIG. 1, the remote exchange component 120a includes an encryption module 130a, the remote exchange component 120b includes an encryption module 130b, and the central exchange component 120c includes an encryption module 130c. Each of the encryption modules can encrypt or decrypt (or both) data that is included in a transmission to or from an additional one of the encryption modules 130a, 130b, or 130c. The encryption modules 130a, 130b, and 130c can use one or more encryption techniques, such as secure communications protocol, public key and/or private key cryptography algorithms using a minimum key size of 128 bits, secure hypertext transfer protocol ("HTTPS"), secure file-transfer protocol ("SFTP"), a secure sockets layer ("SSL"), extended validation SSL certificates, transport layer security ("TLS"), or any other suitable technique for encryption and/or decryption.

In some cases, each of the encryption modules 130a, 130b, and 130c may include one or more instances that are configured to encrypt or decrypt a particular type of data. Examples of a type of data include identity data (e.g., PII), inquiry data (e.g., a request to access secured data), response data (e.g., information that fulfills a request), or any other suitable type of data. In some cases, an exchange component that includes a particular encryption module, or instance of the particular encryption module, is capable of encrypting or decrypting transmissions with an additional exchange component that includes an additional instance of the particular encryption module.

In FIG. 1, one or more of the systems 160, 170, or 180 may securely request or provide access to secured data via the exchange processing system 110. For example, one or more computing systems in the computing environment 100 may include secured data, such as secured data 185 that is stored with the information reporting system 180 or secured data 175 that is stored with the data generation system 170. The secured data may include one or more types of sensitive information or personally identifiable information (e.g., "PIP") that are related to an end-user. For example, the secured data may include PII that describes a person's name, address, social security number, or other identifying information. In addition, the secured data may include sensitive information that describes the person's employment history, medical history, genetic makeup, financial information, educational history, nationality, ethnic heritage, religious affiliation, personal preferences, or other personal characteristics. The secured data may include information that is considered protected, such as any type of information that is protected against unpermitted disclosure by a law, a contractual term, or other agreement. In some cases, the secured data may be generated by one or more computing systems that are under operation of respective organizations that generate sensitive data, such as a hospital, an insurance company, a lending institution, a credit reporting agency, or other suitable organizations. As a non-limiting example, the data generation system 170 could be under operation of a healthcare organization or a financial institution, and the information reporting system 180 could be under operation of a medical recordkeeping organization or a credit reporting agency.

In the computing environment 100, access request data, response data, and other data that are sent via the exchange processing system 110 may be transmitted to or from one of the exchange components included in the exchange processing system 110, such as the exchange components 120a, 120b, or 120c. In addition, data that are sent by the exchange processing system 110 may be encrypted prior to transmission (or decrypted subsequent to receipt) via one of the encryption modules 130a, 130b, and 130c. In some cases, encryption is performed based on a data input received, by the exchange component, from the computing system in which the exchange component is included. Additionally or alternatively, the exchange component need not store unencrypted data that is indicated by the input. In some cases, avoiding storage of data that is not encrypted improves security of the data, such as by reducing a quantity of storage locations.

As a non-limiting example, the central exchange component 120c may receive, from the information reporting system 180, a data input indicating response data 182 (e.g., responding to an access request) and also an encryption input indicating a data key 184 by which the response data 182 is to be encrypted. For instance, if the response data 182 is related to a user of the request initiation system 160, the data key 184 may be a customer ID associated with the user. Upon receipt at an input (e.g., an API port) of the central exchange component 120c, the encryption module 130a may encrypt the response data 182 based on the data key 184. In this example, the central exchange component 120c may retain encrypted response data 115 and discard (or otherwise avoid storage of) the inputted response data 182 and data key 184. The encrypted response data 115 may be transmitted to another exchange component, such as to the remote exchange component 120b. In some cases, the encrypted response data 115 may be transmitted with an indication of the data key 184, such that the indication does not include the data key itself. Responsive to receipt of the encrypted response data 115, the remote exchange component 120b may request, from the data generation system 170, a data key 174 that is associated with the encrypted response data 115. The data key 174 may include information that is identical or similar to information included in the data key 184, such as the customer ID associated with the user. Upon receipt of the data key 174 at an input of the remote exchange component 120b, the encryption module 130b may decrypt the encrypted response data 115 based on the data key 174. In addition, the remote exchange component 120b may provide the decrypted response data 172 to the data generation system 170 and discard (or otherwise avoid storage of) the decrypted response data 172 and the inputted data key 174.

In some aspects, the exchange processing system 110 may securely transmit secured data among included exchange components without storing unencrypted data and without storing a data key by which data is encrypted or decrypted. In some cases, the use of the exchange processing system 110 improves security of the secured data by avoiding transmission or storage of the data key. For instance, if an exchange component receives encrypted data and an indication of a data key, the exchange component may request a local copy of the indicated data key from the computing system in which the exchange component is included. If the computing system does not already possess a local copy of the indicated data key, the encrypted data cannot be decrypted.

Figure 2:
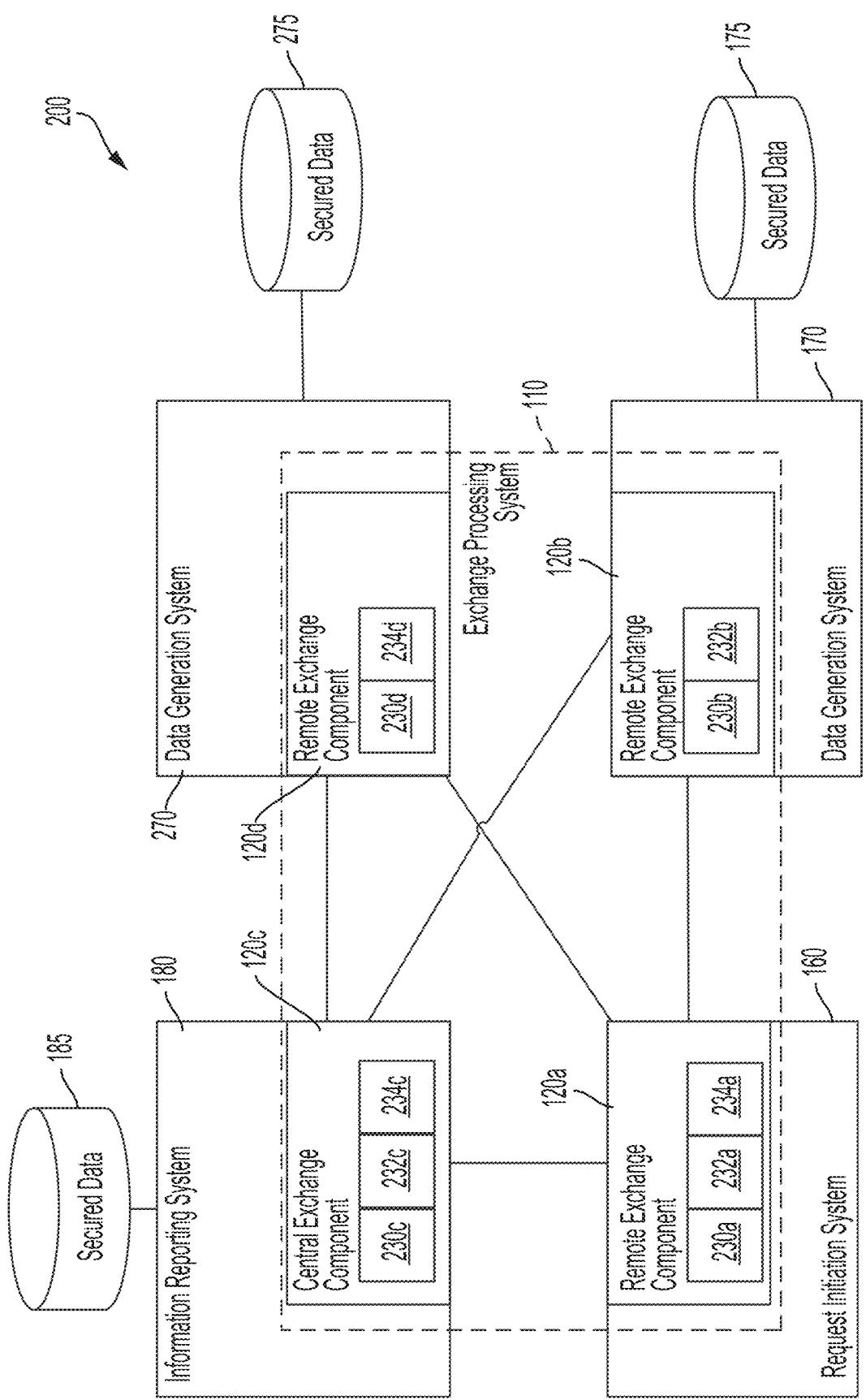
FIG. 2 is a block diagram depicting an example of a computing environment in which multi-instance encryption modules encrypt data exchanged among multiple computing systems, according to certain aspects.

FIG. 2 is a block diagram depicting an example of a computing environment 200 in which multi-instance encryption modules perform encryption of data that is exchanged among multiple computing systems. The multi-instance encryption modules may be included in exchange components of the exchange processing system 110. In addition, the multi-instance encryption modules may be included in multiple computing systems, such as systems that are separate and capable of communicating via a computing network, systems that are under operational control by multiple distinct entities, or computing systems that are otherwise different from each other, as described in regards to FIG. 1.

The exchange processing system 110 includes the central exchange component 120c, the remote exchange component 120a, and the remote exchange component 120b, as described in regards to FIG. 1. In the computing environment 200, the exchange processing system 110 further includes a remote exchange component 120d that is included in a data generation system 270. The data generation system 270 may include secured data, such as secured data 275 that is stored with the system 270. In FIG. 2, the request initiation system 160 may be under operational control of a user, such as a person who is an owner of (or otherwise associated with) at least a portion of one or more of the secured data 185, 175, or 275. In addition, the data generation systems 170 and 270 may be under operational control of respective entities, such as organizations with which the user has a relationship. For example, and not by way of limitation, the data generation systems 170 and 270 may be under operational control of healthcare organizations (e.g., hospitals, insurance companies) that generate medical information for the user. As an additional non-limiting example, the data generation systems 170 and 270 may be under operational control of financial institutions (e.g., banks, credit card companies) that generate financial information for the user. In some cases, the information reporting system 180 may be under operational control of an intermediary organization, such as a medical record management company or a credit reporting agency, that maintains or generates additional information for the user, such as medical records or credit history information. The person who owns the portion of the secured data may use the exchange processing system 110 to securely request access to his or her secured data, the request designating one or more of the data generation systems 170 or 207 as a recipient of the secured data.

In FIG. 2, each of the systems 160, 170, 270, and 180 can communicate, via exchange components in the exchange processing system 110, with at least one additional one of the systems. Communications that are provided or received via the exchange processing system 110 may be encrypted via one or more instances of an encryption module. In the computing environment 200, the central exchange component 120c includes an encryption module instance 230c, and encryption module instance 232c, and an encryption module instance 234c; the remote exchange component 120a includes encryption module instances 230a, 232a, and 234a; the remote exchange component 120b includes encryption module instances 230b and 232b; and the remote exchange component 120d includes encryption module instances 230d and 234d. In some cases, one or more of the instances 230a-230d, 232a-232c, 234a-234b, or 234d may encrypt or decrypt data response to receiving one or more data keys (e.g., data key 184, data key 174) from the respective computing system 160, 170, 180, or 270 in which the instance is included.

In the computing environment 200, a particular instance of a multi-instance encryption module may be instantiated (or otherwise generated) for a particular exchange component that is included in a particular computing system. The particular encryption module instance may be associated with the particular exchange component and particular computing system. For example, the particular encryption module instance could be instantiated based on information received from one or more of the associated exchange component or associated computing system. The information could be used, for example, to generate a particular encryption/decryption key for the particular instance, to generate authorization data identifies the associated exchange component or associated computing system, or to complete other suitable instantiation processes. In addition, the particular instance of the multi-instance encryption module can perform encryption or decryption functions for the associated exchange component. For example, the particular instance can receive system-specific data that indicates one or more of the associated exchange component or associated computing system. The particular instance can encrypt data for that particular exchange component, decrypt data for that particular exchange component, or both. In addition, the particular instance can be prevented from performing operations with respect to an additional exchange component other than the associated exchange component for that instance. For example, the instance 230a can perform encryption or decryption functions for the remote exchange component 120a responsive to receiving, from the exchange component 120a, system-specific data (e.g., authorization data, data describing an identity of the component 120a or the system 160). In addition, if the system-specific data for the component 120a or the system 160 is not received, the instance 230a can cease or forgo encryption or decryption functions (e.g., by ignoring commands or data received without the system-specific data). In some cases, the instance 230a may perform additional functions if the system-specific data is not received, such as transmitting an alert to the central exchange component 120c. In some aspects, an encryption module instance that is configured for an associated exchange component included in an associated system may improve security of the exchange processing system 110, such as by reducing opportunities for a malicious actor to copy, hijack, or otherwise misuse the encryption module instance.

In some cases, each exchange component includes a respective instance of a first multi-instance encryption module, such that each exchange component is capable of encrypting or decrypting data from any other exchange component included in the exchange processing system 110. In FIG. 2, encryption module instances 230a, 230b, 230c, and 230d are instances of a first multi-instance encryption module. Each of the exchange components 120a, 120b, 120c, and 120d are capable of encrypting or decrypting, via the respective included instances 230a, 230b, 230c, and 230d, data that is transmitted to or from another one of the exchange components. In some cases, the first multi-instance encryption module is an identity encryption module that is configured to encrypt or decrypt identity data, such as data describing PII. For example, the remote exchange component 120a may encrypt, via the instance 230a, identity data received from the request initiation system 160, such as identity data describing a request. The remote exchange component 120a may transmit the encrypted identity data to the central exchange component 120c via the exchange processing system 110. In addition, the central exchange component 120c may decrypt, via the instance 230c, the encrypted identity data, and provide the decrypted identity data to the information reporting system 180, such as to fulfill the request. In some cases, the remote exchange components 120b and 120d may decrypt the encrypted identity data via respective instances 230b and 230d, such as if the encrypted identity data were transmitted to them via the exchange processing system 110.

In addition, one or more exchange components include respective instances of an additional multi-instance encryption module, such that the one or more exchange components are capable of encrypting or decrypting data from another exchange component that has another instance of the additional multi-instance encryption module. In some cases, the additional multi-instance encryption module is included in a sub-set of the exchange components, such that not all exchange components on the exchange processing system 110 are capable of encrypting or decrypting data via the additional multi-instance encryption module. In FIG. 2, encryption module instances 232a, 232b, and 232c are instances of a second multi-instance encryption module. Each of the exchange components 120a, 120b, and 120c are capable of encrypting or decrypting, via the respective included instances 232a, 232b, and 232c, data that is transmitted to or from another exchange component having an instance of the second multi-instance encryption module. In addition, encryption module instances 234a, 234c, and 234d are instances of a third multi-instance encryption module. Each of the exchange components 120a, 120c, and 120d are capable of encrypting or decrypting, via the respective included instances 234a, 234c, and 234d, data that is transmitted to or from another exchange component having an instance of the third multi-instance encryption module. In some cases, the additional multi-instance encryption module is a request encryption module that is configured to encrypt or decrypt data describing an access request, such as inquiry data including a request to access secured data, response data including information that fulfills a request, data indicating a data key by which the access request data is encrypted (e.g., an indication that omits the data key itself), or other suitable data describing an access request. In some cases, the request encryption module can avoid encrypting or decrypting identity data. In addition, an identity encryption module can avoid encrypting or decrypting access request data.

In some aspects, an access request may include multiple request parts, such as one or more of an inquiry, a confirmation of the request, a response, an acknowledgment of completion, or another suitable part of the request. In some cases, the access request, or a part of an access request, is transmitted among two or more particular exchange components that include instances of a particular multi-instance encryption module. In addition, an exchange component may select a particular encryption module instance, e.g., for encryption or decryption of the access request part, based on an additional exchange component that provides or receives the request part. Furthermore, an exchange component may receive or provide the request part via a particular input or output, based on the additional exchange component that provides or receives the request part. For instance, the central exchange component 120c may encrypt data that is intended for the remote exchange component 120b. Based on a determination that the component 120b is the recipient, the central exchange component 120c may select the instance 232c for encryption of the data. In addition, the encrypted data may be provided to the remote exchange component 120b via a first input, such as a first API port that is shared with the component 120b. In an additional example, responsive to determining that remote exchange component 120d is the recipient, the central exchange component 120c may select the instance 234c for encryption of the data, and provide the encrypted data to the component 120d via a second input, such as a second API port that is shared with the component 120d.

Figure 3:
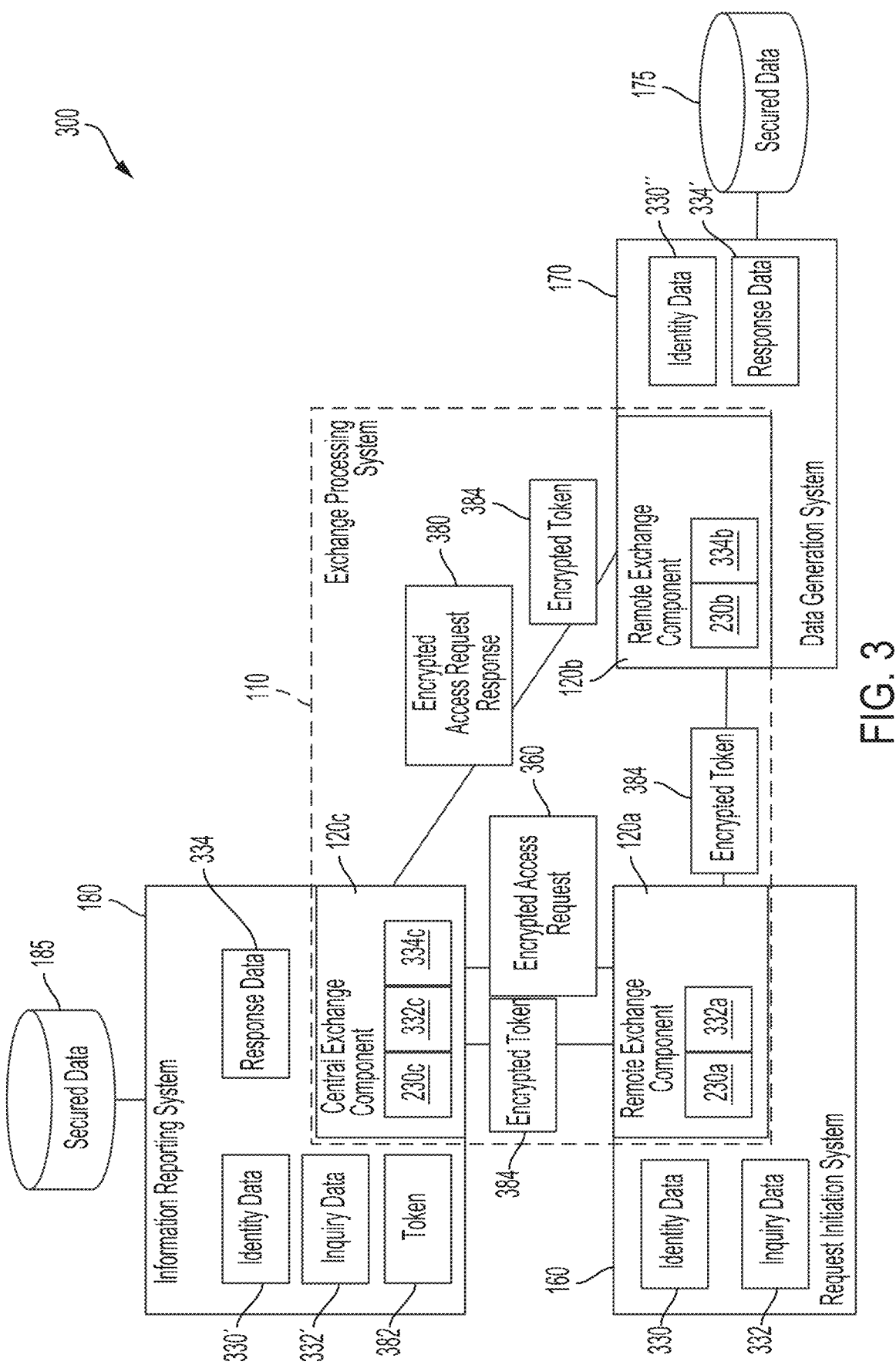
FIG. 3 is a block diagram depicting an example of a computing environment in which an exchange processing system implements a multi-system request to access secured data, according to certain aspects.

FIG. 3 is a block diagram depicting an example of a computing environment 300, in which an exchange processing system implements a multi-system request to access secured data. The multi-system access request may include multiple request parts that are transmitted among two or more computing systems in the environment 300. In some cases, the multi-system request may include a multi-system authentication of the access request, such as authentication information that is provided by each computing system that participates in the multi-system access request.

The computing environment 300 includes the request initiation system 160, the data generation system 170 having secured data 175, and the information reporting system 180 having secured data 185, as described in regards to FIGS. 1-2. The computing environment 300 also includes the exchange processing system 110, which includes the central exchange component 120c, the remote exchange component 120a, and the remote exchange component 120b, as described in regards to FIGS. 1-2. In some cases, the computing environment 300 includes one or more additional computing systems (such as the data generation system 270), remote exchange components (such as the remote exchange component 120d), or encryption module instances (such as, e.g., instances 232a-232d, 234a, 234c-234d) but for simplicity and not by way of limitation, FIG. 3 does not depict these.

In the computing environment 300, the exchange processing system 110 includes the central exchange component 120c with encryption module instances 230c, 332c, and 334c; the remote exchange component 120a with encryption module instances 230a and 332a; and the remote exchange component 120b with encryption module instances 230b and 334b. In FIG. 3, the encryption module instances 230a, 230b, and 230c are instances of an identity encryption module, as described in regards to FIGS. 1-2. In addition, the encryption module instances 332a and 332c are instances of a first request encryption module, and the encryption module instances 334b and 334c are instances of a second request encryption module. In some cases, one or more of the instances 230a-230c, 332a, 332c, or 334b-334c may encrypt or decrypt data responsive to receiving one or more data keys (e.g., data key 184, data key 174) from the respective computing system 160, 170, or 180 in which the instance is included.

In FIG. 3, the exchange processing system 110 may securely transmit request parts of a multi-system access request. In an aspect, the request initiation system 160 may generate a request to access a portion of the secured data 185. For instance, responsive to input received via a user interface or other suitable input technique, the request initiation system 160 may generate (or otherwise receive) one or more of identity data 330 or inquiry data 332. The identity data 330 may include PII that indicates a requestor that desires to enable access to the secured data, such as a person operating the request initiation system 160. The inquiry data 332 may include data describing the access request. For instance, the inquiry data 332 could include data describing the desired portion of the secured data 185, a recipient of the accessed data, a time frame of the request, or other suitable data describing the access request. As a non-limiting example, if the secured data 185 includes medical records, the identity data 330 could include a patient ID, and the inquiry data 332 could indicate medical records related to a particular medical procedure, a computing system of an insurance company that is the recipient of the requested medical records, and a duration of time (e.g., one day, two weeks) during which the requested data is available to the recipient.

The request initiation system 160 may provide the identity data 330 and the inquiry data 332 to the exchange processing system 110 via the remote exchange component 120*a*. In some cases, each of the identity data 330 and the inquiry data 332 may be received via respective inputs of the remote exchange component 120*a*, such as an API port for the identity data 330 and an additional API port for the inquiry data 332. Responsive to receiving the data 330 and 332, the remote exchange component 120*a* may select an instance of an encryption module to encrypt each of the identity data 330 and the inquiry data 332. For instance, responsive to receiving the identity data 330 via a first input, the remote exchange component 120*a* may encrypt the identity data 330 via the encryption module instance 230*a* (e.g., an instance of the identity encryption module). Responsive to receiving the inquiry data 332 via a second input, the remote exchange component 120*a* may encrypt the inquiry data 332 via the encryption module instance 332*a* (e.g., an instance of the first request encryption module). In some cases, the identity data 330 and the inquiry data 332 are not stored or otherwise retained by the remote exchange component 120*a*. In some aspects, avoiding storage of the data 330 or 332 improves security of the data 330 and 332, such as by reducing network-accessible storage locations of sensitive data.

In addition, the remote exchange module 120*a* may generate an encrypted access request 360, which includes the encrypted identity data based on the data 330 and the encrypted inquiry data based on the data 332. The encrypted access request 360 may be transmitted from the remote exchange module 120*a* to the central exchange component 120*c* via a secured channel included in the exchange processing system 110. Responsive to receiving the encrypted access request 360, the central exchange component 120*c* may select an instance of an encryption module to decrypt some or all of the encrypted access request 360. For example, the central exchange component 120*c* may decrypt a first part of the encrypted request 360, which is indicated as representing identity data, via the encryption module instance 230*c* (e.g., an instance of the identity encryption module). In addition, the central exchange component 120*c* may decrypt a second part of the encrypted request 360, which is indicated as representing inquiry data, via the encryption module instance 332*c* (e.g., an instance of the first request encryption module). In some aspects, the decrypted parts of the encrypted request 360 are provided to the information reporting system 180 via respective outputs of the central exchange component 120*c*, such as respective API ports. The information reporting system 180 may generate identity data 330' and inquiry data 332' based on, respectively, the decrypted first part and decrypted second part of the encrypted request 360. In some cases, the identity data 330' and inquiry data 332' are not stored or otherwise retained by the central exchange component 120*c*, which may improve security of the data 330' and 332' by reducing network-accessible storage locations of sensitive data.

In FIG. 3, the information reporting system 180 may select some or all of the secured data 185, based on the identity data 330' and inquiry data 332'. As a non-limiting example, the information reporting system 180 may select a part of the data 185 that is associated with a patient ID described by the identity data 330'. The example selection may also be based on a determination that a recipient described by the inquiry data 332', such as the data generation system 170, is authorized to receive the secured data part, or a particular transformation of the secured data part.

In some cases, the information reporting system 180 may request additional secured data from one or more additional computing systems. As a non-limiting example, if the inquiry data 332 and 332' indicate that a credit score is requested, the information reporting system 180 may generate and provide to the component 120*c* additional access requests for additional computing systems that are operated by financial institutions. The additional access requests may be provided, via the exchange processing system 110, to respective remote exchange components included in the additional computing systems. Via the respective remote exchange components, the additional computing systems may provide additional secured data that is encrypted or transformed (or both) to the central exchange component 120*c*. In addition, the central exchange component 120*c* may decrypt the additional secured data, and provide the decrypted additional data to the information reporting system 180. In this example, the information reporting system 180 may generate a part of the selected data based on the decrypted additional data (e.g., generating a credit score based on transformed financial information), or may include a part of the decrypted additional data in the selected data.

The information reporting system 180 may generate response data 334 from the selected data (e.g., retrieved from secured data 185, generated based on received data). In some aspects, the response data 334 may include at least a part of the selected data. In addition, the response data 334 may include transformed data that represents the selected data. In some cases, the transformed data represents the selected data without including the selected data. For example, if the selected data represents data about a medical procedure, the transformed data may include a billing code that does not describe the medical procedure. In some cases, the response data 334 may include transformed data and omit the selected part of the secured data 185. In some aspects, generating a response that includes transformed data and omits secured data improves security of the secured data, such as by avoiding transmission of the secured data between computing systems.

The information reporting system 180 may provide one or more of the response data 334 or the identity data 330' to the exchange processing system 110 via the central exchange component 120c. In some cases, each of the response data 334 or the identity data 330' may be received via respective inputs of the central exchange component 120c, such as respective API ports. Responsive to receiving the data 334 and 330', the central exchange component 120c may select an instance of an encryption module to encrypt each of the response data 334 and the identity data 330'. For instance, responsive to receiving the identity data 330' via a first input and the response data 334 via a second input, the central exchange component 120c may encrypt the identity data 330' via the encryption module instance 230c and the response data 334 via the encryption module instance 334c (e.g., an instance of the second request encryption module). In some cases, the response data 334 and the identity data 330' are not stored or otherwise retained by the central exchange component 120c, which may improve security of the data 334 and 330' by reducing network-accessible storage locations of sensitive data.

In FIG. 3, the central exchange component 120c may generate an encrypted access response 380. The encrypted response 380 may include the encrypted identity data based on the data 330' and the encrypted response data based on the data 334. The encrypted access request response 380 may be transmitted from the central exchange module 120c to the remote exchange component 120b via an additional secured channel included in the exchange processing system 110. Responsive to receiving the encrypted access request response 380, the remote exchange component 120b may select an instance of an encryption module to decrypt some or all of the encrypted access request response 380. For example, the remote exchange component 120b may decrypt a first part of the encrypted request 380, which is indicated as representing identity data, via the encryption module instance 230b (e.g., an instance of the identity encryption module). In addition, the remote exchange component 120b may decrypt a second part of the encrypted request 380, which is indicated as representing response data, via the encryption module instance 334b (e.g., an instance of the second request encryption module). In some aspects, the decrypted parts of the encrypted request 380 are provided to the data generation system 170 via respective outputs of the remote exchange component 120b, such as respective API ports. The data generation system 170 may generate identity data 330" and response data 334' based on, respectively, the decrypted first part and decrypted second part of the encrypted response 380. In some cases, the identity data 330" and response data 334' are not stored or otherwise retained by the remote exchange component 120b. which may improve security of the data 330" and 334' by reducing network-accessible storage locations of sensitive data.

In some aspects, accessing the secured data is based on a multi-party authentication, such as authentication information that is provided by each computing system that participates in the multi-system access request. For instance, the information reporting system 180 may generate an authentication token 382 subsequent to receiving the identity data 330' and inquiry data 332' from the central exchange component 120c. The token 382 may include information that is associated with the access request, such as data identifying the information reporting system 180, the inquiry data 332', or other suitable information. The token 382 may be provided to the central exchange component 120c. Based on the token 382, the central exchange component 120c may generate an encrypted token 384 via an encryption module instance that is associated with the remote exchange component 120b, such as the instance 334c of the second request encryption module. In some cases, encrypted identity data may accompany the encrypted token 384, such as encrypted identity data based on the identity data 330' that is encrypted by the encryption module instance 230c.

The central exchange component 120c may provide the encrypted token 384 to the remote exchange component 120a, which may provide the encrypted token 384 to the remote exchange component 120b. In some cases, the remote exchange component 120a may decrypt or re-encrypt the encrypted token 384, and provide the re-encrypted token to the remote exchange component 120b. Responsive to receiving the encrypted token 384, the remote exchange component 120b may provide the encrypted token 384 to the central exchange component 120c. In some cases, the remote exchange component 120b may decrypt or re-encrypt the encrypted token 384, such as via the encryption module instance 334b, and provide the re-encrypted token to the central exchange component 120c.

The central exchange component 120c may decrypt the encrypted token via the instance 334c, and provide the decrypted token to the information reporting system 180. Responsive to determining that the decrypted token (e.g., from encrypted token 384 received from the remote exchange component 120b) matches the token 382 (e.g., generated by the information reporting system 180), the information reporting system 180 may generate the response data 334 based on the selected part of the secured data 185. In some aspects, generating the response data 334 responsive to determining a match between the generated token 382 and the encrypted token 384 received from the remote exchange component 120b provides multi-party authentication for the exchange processing system 110. In some cases, multi-party authentication may improve security of the exchange processing system 110, such as by providing an authentication technique for verifying each computing system that is a party to an access request.

Figure 4:
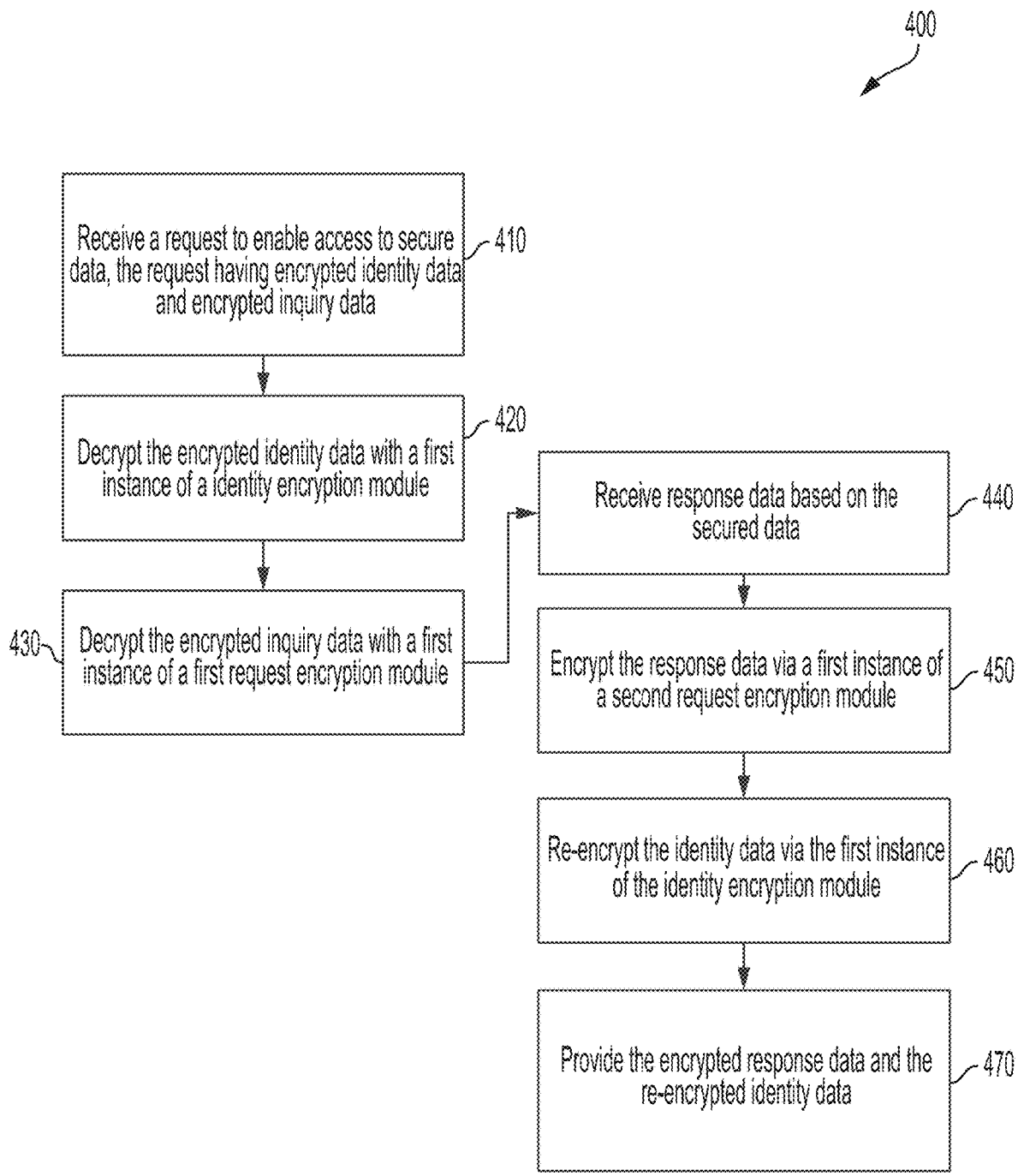
FIG. 4 is a flow chart depicting an example of a process for a multi-system request to access secure data, according to certain aspects.

FIG. 4 is a flow chart depicting an example of a process 400 for a multi-system request to access secure data. In some aspects, such as described in regards to FIGS. 1-3, one or more computing devices executing an exchange processing system implements operations described in FIG. 4, by executing suitable program code. For illustrative purposes, the process 400 is described with reference to the examples depicted in FIGS. 1-3. Other implementations, however, are possible.

At block 410, the process 400 involves receiving a request to enable access to secure data. In some cases, the request may include encrypted identity data that is encrypted via a first instance of an identity encryption module. Additionally or alternatively, the request may include encrypted inquiry data that is encrypted via a first instance of a first request encryption module. The request may be received by a central exchange component and received from a remote exchange component, each of which is included in an exchange processing system. For example, the central exchange component 120c in the exchange processing system 110 may receive the encrypted access request 360 from the remote exchange component 120a. In addition, the encrypted access request 360 may include encrypted identity data that was encrypted via the identity encryption module instance 230a, and encrypted inquiry data that was encrypted via the request encryption module instance 332a.

At block 420, the process 400 involves decrypting the encrypted identity data. The encrypted identity data may be decrypted via a second instance of the identity encryption module. At block 430, the process 400 involves decrypting the encrypted inquiry data. The encrypted inquiry data may be decrypted via a second instance of the first request encryption module. For example, the central exchange component 120*c* may decrypt the identity data in the encrypted access request 360 via the identity encryption module instance 230*c*. In addition, the central exchange component 120*c* may decrypt the inquiry data in the encrypted access request 360 via the first request module instance 332*c*.

At block 440, the process 400 involves receiving response data that is based on at least a portion of the secured data. The response data may be generated from a selected portion of the secure data. In addition, the selected portion of the secure data may be accessed based on one or more of the decrypted identity data or the decrypted inquiry data. For example, the central exchange component 120*c* may receive, from the information reporting system 180, the response data 334. The response data 334 may be accessed by the information reporting system 180 based on one or more of the identity data 330' and the inquiry data 332'.

In some aspects, the response data is received, accessed, or both responsive to authentication information that is received from an additional exchange component included in the exchange processing system. For example, the central exchange component 120*c* may receive the encrypted token 384 from the remote exchange component 120*b*. In addition, the central exchange component 120*c* may decrypt the encrypted token 384 and provide the decrypted token to the information reporting system 180. Responsive to receiving the decrypted token, the information reporting system 180 may perform one or more of accessing the secured data 185 or providing the response data 334 to the central exchange component 120*c*.

At block 450, the process 400 involves encrypting the response data via a first instance of a second request encryption module. At block 460, process 400 involves re-encrypting the identity data via the second instance of the identity encryption module. For example, the central exchange component 120*c* may encrypt the response data 334 via the second request encryption module instance 334*c*. In addition, the central exchange component 120*c* may re-encrypt the identity data 330' via the identity encryption module instance 230*c*.

At block 470, the process 400 involves providing, from the central exchange component, the encrypted response data and the re-encrypted identity data. The encrypted response data and the re-encrypted identity data may be provided to an additional remote exchange component in the exchange processing system. For example, the central exchange component 120*c* may provide the encrypted access request response 380 to the remote exchange component 120*b*. In addition, the encrypted access request response 380 may include the encrypted identity data that was re-encrypted via the identity encryption module instance 230*c* and the encrypted response data that was encrypted via the second request encryption module instance 334*c*. In some cases, the additional remote exchange component is configured to decrypt the encrypted response data via a second instance of the second request encryption module and to decrypt the re-encrypted identity data via a third instance of the identity encryption module. For instance, based on the encrypted access request response 380, the remote exchange component 120*b* may decrypt the encrypted response data and the re-encrypted identity data via, respectively, the second request encryption module instance 334*b* and the identity encryption module instance 230*b*.

In some aspects, an exchange processing system with multiple remote exchange components may update a first remote exchange component based on a modification performed at a second remote exchange component. For example, if the second remote exchange component modifies a data transformation technique (e.g., based on a learned modification for the transmission technique), update information indicating the modified technique may be received by the first remote exchange component. Responsive to receiving the update information, the first remote exchange component may modify a local instance of the data transformation technique.

Figure 5:
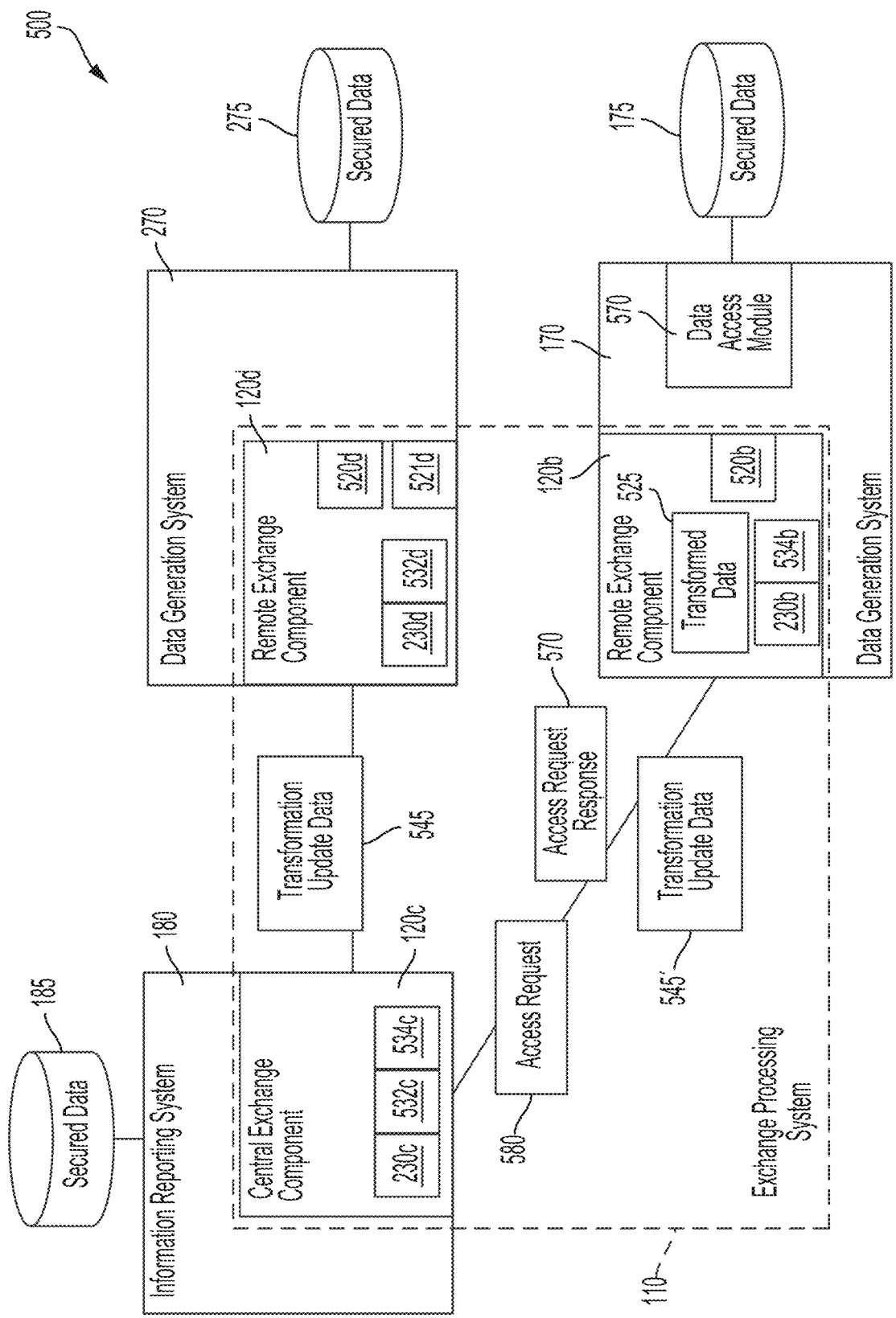
FIG. 5 is a block diagram depicting an example of a computing environment in which multiple exchange components are updated based on a modification from a particular one of the exchange components, according to certain aspects.

FIG. 5 is a block diagram depicting an example of the computing environment 500, in which multiple remote exchange components in an exchange processing system are updated based on a modification from a particular one of the remote exchange components. In some cases, the modification may be to a transformation technique that is applied to secured data received by the particular remote exchange component. In addition, the modification may be learned by the particular one of the remote exchange components, such as by a neural network configured to determine modifications to the transformation technique.

The computing environment 500 includes the information reporting system 180 having secured data 185, the data generation system 170 having secured data 175, and the data generation system 270 having secured data 275, as described in regards to FIGS. 1-4. The computing environment 500 also includes the exchange processing system 110, which includes the central exchange component 120*c*, the remote exchange component 120*b*, and the remote exchange component 120*d*, as described in regards to FIGS. 1-4. In some cases, the computing environment 500 includes one or more additional computing systems (such as the request initiation system 160), remote exchange components (such as the remote exchange component 120*a*), or encryption module instances, but for simplicity and not by way of limitation, FIG. 5 does not depict these.

In the computing environment 500, the exchange processing system 110 includes the central exchange component 120*c* with encryption module instances 230*c*, 532*c*, and 534*c*; the remote exchange component 120*b* with encryption module instances 230*b* and 534*b*; and the remote exchange component 120*d* with encryption module instances 230*d* and 532*d*. In FIG. 5, the encryption module instances 230*a*, 230*b*, and 230*c* are instances of an identity encryption module, as described in regards to FIGS. 1-4. In addition, the encryption module instances 534*b* and 534*c* are instances of a first request encryption module, and the encryption module instances 532*d* and 532*c* are instances of a second request encryption module (e.g., such as the first and second request encryption modules described in regards to FIG. 3). In some cases, one or more of the instances 230*b*-230*d*, 532*c*-532*d*, or 534*b*-534*c* may encrypt or decrypt data responsive to receiving one or more data keys (e.g., data key 184, data key 174) from the respective computing system 170, 180, or 270 in which the instance is included.

In FIG. 5, the exchange processing system 110 may securely transmit request parts of a multi-system access request, such as described in regards to FIGS. 1-4. In an aspect, the central exchange component 120*c* may provide to the remote exchange component 120*b* an access request 580. The access request 580 may include one or more of identity data that is encrypted via the instance 230*c* or inquiry data that is encrypted via the instance 534*c*. In addition, the encrypted inquiry data may describe a requested portion of the secured data 175.

Responsive to receiving the access request 580, the remote exchange component 120*b* may decrypt the encrypted inquiry data via the instance 534*b*. In addition, the remote exchange component 120*b* may provide the decrypted inquiry data to a data access module 570 that is included in the data generation system 170. The data access module 570 includes program code that is executable by one or more processing devices of the computing system in which the data access module 570 is included (e.g., the data generation system 170). In addition, the data access module 570 may receive operational control from the data generation system 170, such as programming instructions that indicate interactions with a remote exchange component that is under operational control of an additional computing system (e.g., the remote exchange component 120*b* which receives operational control information via the central exchange component 120*c*).

In some cases, the decrypted inquiry data is provided to the data access module 570 via an output (e.g., a first API port) of the remote exchange component 120*b*. The data access module 570 may determine, based on the decrypted inquiry data, the requested portion of the secured data 175, and access the requested data. In some cases, the data access module 570 may generate additional requests to access additional secured data, and provide the additional requests to additional computing systems via the exchange processing system 110, such as described in regards to FIGS. 1-4. In addition, the remote exchange component 120*b* may receive, from the access module 570, the requested secured data via an input (e.g., a second API port) of the component 120*b*.

Responsive to receiving the secured data, the remote exchange component 120*b* may transform the secured data by applying a transformation module 520*b*. In some cases, the input by which the secured data is received is an input to the transformation module 520*b*. The transformation module 520*b* may generate transformed data 525 by modifying the secured data via a transformation technique. For example, the transformed data 525 may represent the requested secured data, such as a representation by an identification code (e.g., a billing code), a grouping (e.g., binning of data), or another suitable representation type. In addition, the transformed data 525 may omit the requested secured data. In some cases, generating transformed data that includes a representation of secured data and omits the secured data itself may improve security of the secured data, such as by avoiding storage of the secured data at a network-accessible location.

In the computing environment 500, the remote exchange component 120*b* may generate an access request response 570 based on the transformed data 525. The access request response 570 may include encrypted transformed data, such as an encryption of the transformed data 525 via the first request encryption module instance 534*b*. In addition, the access request response 570 may include encrypted identity data, such as identity data encrypted via the identity encryption module instance 230*b*. The remote exchange component 120*b* may provide the access request response 570 to the central exchange component 120*c*.

In an aspect, the remote exchange component 120*b* may update the transformation module 520*b* based on update data generated by another remote exchange component included in the exchange processing system 110. In the computing environment 500, the remote exchange component 120*d* may include an additional transformation module 520*d*. The remote exchange component 120*d* may determine a modification to the transformation module 520*d*, such as a modification that changes the transformation technique used by the module 520*d*. As an example, and not by way of limitation, a learning module 521*d* included in the remote exchange component 120*d* may determine a learned modification to the transformation module 520*d*, such as a learned modification that improves security, efficiency, or other characteristics of the transformation technique. In some cases, the learning module 521*d* may include one or more neural networks.

In FIG. 5, the remote exchange component 120*d* may generate transformation update data 545 that describes the modification to the transformation module 520*d*. In some cases, the transformation update data 545 is encrypted via the second request encryption module instance 532*d*. The remote exchange component 120*d* may provide the transmission update data 545 to the central exchange component 120*c*. The central exchange component 120*c* may decrypt the transformation update data 545 via the instance 532*c*. In addition, the central exchange component 120*c* may determine that the modification described by the transformation update data 545 corresponds to one or more additional exchange components in the exchange processing system 110. For example, the central exchange component 120*c* may determine that the modification corresponds to the transformation module 520*b* included in the remote exchange component 120*b*. In addition, the central exchange component 120*c* may generate additional transformation update data 545' that describes the modification. In some cases, the transformation update data 545' may include data describing a localization of the modification, such as a localization that is suitable to a computing system (e.g. the data generation system 170) on which the transmission module 520*b* operates. The central exchange component 120*c* may provide the transformation update data 545' to the remote exchange component 120*b*. In some cases, the transformation update data 545' may be encrypted via the instance 534*c*. In addition, the remote exchange component 120*b* may decrypt the encrypted transformation update data 545' via the instance 534*b*.

Responsive to receiving the transformation update data 545', the remote exchange component 120*b* modifies the transformation module 520*b*. For example, the modification includes changing the transformation technique used by the module 520*b* to include the learned modification that was included in the transmission module 520*d*. In some aspects, providing multiple remote exchange components with update data indicating a learned modification improves security or efficiency of multiple transformation module included in the multiple remote exchange components, such as by quickly distributing to the multiple components a modification learned at a particular one of the remote exchange components.

Figure 6:
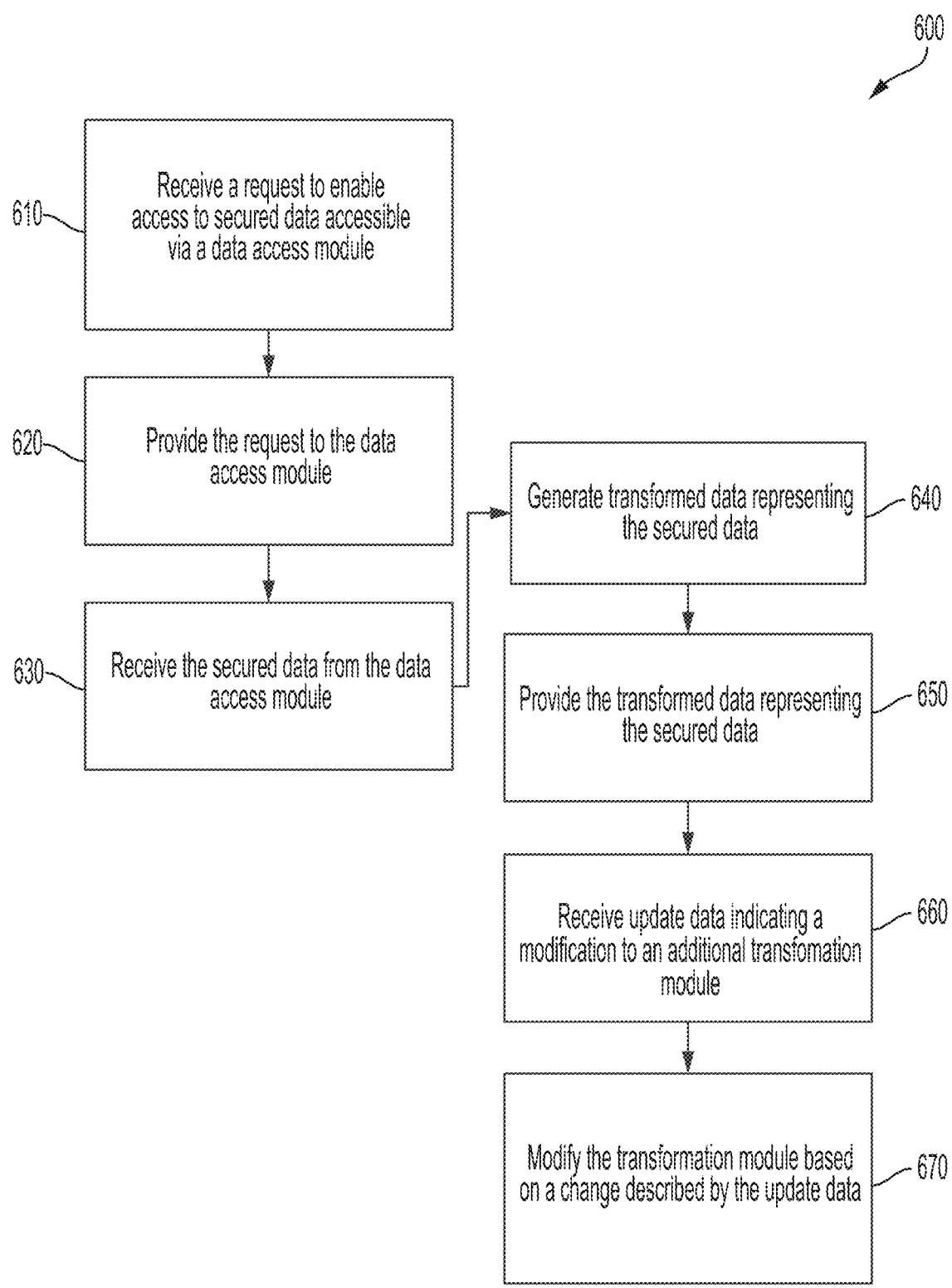
FIG. 6 is a flow chart depicting an example of a process for updating multiple exchange components based on a modification from a particular one of the exchange components, according to certain aspects.

FIG. 6 is a flow chart depicting an example of a process 600 for updating multiple remote exchange components in an exchange processing system based on a modification from a particular one of the remote exchange components. In some aspects, such as described in regards to FIGS. 1-5, a one or more computing devices executing an exchange processing system implements operations described in FIG. 6, by executing suitable program code. For illustrative purposes, the process 600 is described with reference to the examples depicted in FIGS. 1-5. Other implementations, however, are possible.

At block 610, the process 600 involves receiving a request to enable access to secure data that is accessible via a data access module. The request may be received by a remote exchange component and received from a central exchange component, each of which is included in an exchange processing system. For example, the remote exchange component 120*b* may receive the access request 580 from the central exchange component 120c. In addition, the access request 580 may indicate a request to access a portion of the secure data 175 via the data access module 570.

At block 620, the process 600 involves providing the request to the data access module. In some cases, the access request is provided via an output of the remote exchange component. For instance, the remote exchange component 120b may provide the request to the data access module 570 via an output of the component 120b.

At block 630, the process 600 involves receiving the requested secured data from the data access module. In some cases, the secured data is received via an input of the remote exchange component. For example, the remote exchange component 120b may receive the requested secured data via an input port that is accessible by the data access module 570.

At block 640, the process 600 involves generating transformed data via a transformation module of the remote exchange component. The generated transformed data may represent the secured data. The transformed data may be generated responsive to receiving the secured data via the input port. At block 650, the process 600 involves providing the transformed data that represents the secure data. The transformed data may be provided by the remote exchange component to the central exchange component. For example, the transformation module 520b may generate the transformed response data 525 responsive to receiving the secure data from the data access module 570. In addition, the remote exchange component 120b may provide the transformed response data 525, or the access request response 570 based on the transformed data 525, to the central exchange component 120c. In some cases, the remote exchange component 120b encrypts the transformed response data 525 via the first request encryption module instance 534b. The access request response 570 may be based on the encrypted transformed response data 525.

At block 660, the process 600 involves receiving update data indicating a modification to an additional transformation module of an additional remote exchange component that is included in the exchange processing system. For example, the central exchange component 120c may receive the transformation update data 545 from the remote exchange component 120d. The transformation update data 545 may indicate a modification to the transformation module 520d included in the remote exchange component 120d. In addition, the remote exchange component 120b may receive from the central exchange component 120c the transformation update data 545', indicating the modification to the transformation module 520d.

At block 670, the process 600 involves modifying the transformation module to transform data based on the change described by the update data. For example, the remote exchange component 120b may modify the transformation module 520b based on the transformation update 545'. The modified transformation module 520b may perform a transformation of data based on the change described by the transformation update 545'.

Figure 7:
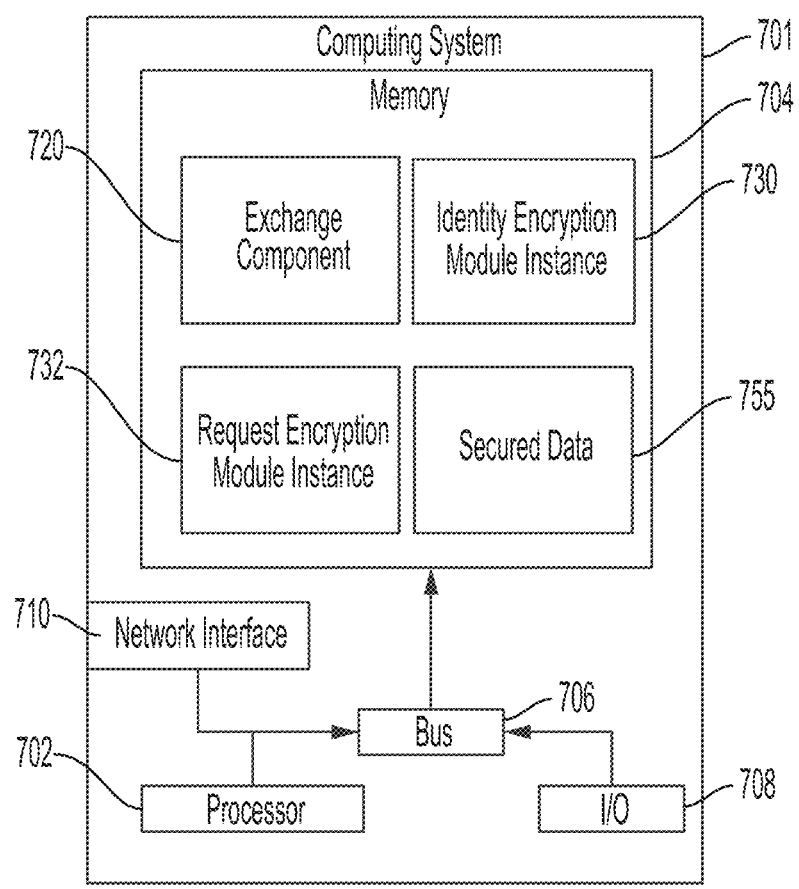
FIG. 7 is a block diagram depicting an example of a computing system configured to implement an exchange module of an exchange processing system, according to certain aspects.

Any suitable computing system or group of computing systems can be used for performing the operations described herein. For example, FIG. 7 is a block diagram depicting a computing system 701 that is configured to include an exchange module of an exchange processing system, according to certain aspects. Examples of the computing system 701 may include one or more of the information reporting system 180, request initiation system 160, or the data generation systems 170 or 270.

The depicted example of a computing system 701 includes one or more processors 702 communicatively coupled to one or more memory devices 704. The processor 702 executes computer-executable program code or accesses information stored in the memory device 704. Examples of processor 702 include a microprocessor, an application-specific integrated circuit ("ASIC"), a field-programmable gate array ("FPGA"), or other suitable processing device. The processor 702 can include any number of processing devices, including one.

The memory device 704 includes any suitable non-transitory computer-readable medium for storing an exchange component 720, an identity encryption module instance 730, a request encryption module instance 732, secured data 755, and other received or determined values or data objects. Examples of the exchange component 720 may include one or more of the central exchange component 120c or the remote exchange modules 120a, 120b, or 120d. Examples of the identity encryption module instance 730 may include one or more of the identity encryption module instances 230a-230d. Examples of the request encryption module instance 732 may include one or more of the request encryption module instances 232a-232c, 234a-234b, 234d, 332a, 332c, 334b-334c, 532c-532d, or 534b-534c. Although FIG. 7 depicts the secured data 755 as running as a program in the memory 704 of computing system 701, other aspects are possible, including the computing system 701 communicating with the secured data 755 via one or more data networks.

In the memory device 704, the computer-readable medium can include any electronic, optical, magnetic, or other storage device capable of providing a processor with computer-readable instructions or other program code. Non-limiting examples of a computer-readable medium include a magnetic disk, a memory chip, a ROM, a RAM, an ASIC, optical storage, magnetic tape or other magnetic storage, or any other medium from which a processing device can read instructions. The instructions may include processor-specific instructions generated by a compiler or an interpreter from code written in any suitable computer-programming language, including, for example, C, C++, C #, Visual Basic, Java, Python, Perl, JavaScript, and ActionScript.

The computing system 701 may also include a number of external or internal devices such as input or output devices. For example, the computing system 701 is shown with an input/output ("I/O") interface 708 that can receive input from input devices or provide output to output devices. A bus 706 can also be included in the computing system 701. The bus 706 can communicatively couple one or more components of the computing system 701.

The computing system 701 executes program code that configures the processor 702 to perform one or more of the operations described above with respect to FIGS. 1-6. The program code includes operations related to, for example, one or more of the exchange component 720, the identity encryption module instance 730, the request encryption module instance 732, the secured data 755, or other suitable applications or memory structures that perform one or more operations described herein. The program code may be resident in the memory device 704 or any suitable computer-readable medium and may be executed by the processor 702 or any other suitable processor. In some aspects, the program code described above, the exchange component 720, the identity encryption module instance 730, the request encryption module instance 732, and the secured data 755 are stored in the memory device 704, as depicted in FIG. 7. In additional or alternative aspects, one or more of the exchange component 720, the identity encryption module instance 730, the request encryption module instance 732, the secured data 755, and the program code described above are stored in one or more memory devices accessible via a data network, such as a memory device accessible via a cloud service.

The computing system 701 depicted in FIG. 7 also includes at least one network interface 710. The network interface 710 includes any device or group of devices suitable for establishing a wired or wireless data connection to one or more data networks. Non-limiting examples of the network interface 710 include an Ethernet network adapter, a modem, and/or the like. The computing system 701 is able to communicate with one or more additional computing systems using the network interface 710, such as an additional computing system that includes an additional exchange component.

General Considerations

Numerous specific details are set forth herein to provide a thorough understanding of the claimed subject matter. However, those skilled in the art will understand that the claimed subject matter may be practiced without these specific details. In other instances, methods, apparatuses, or systems that would be known by one of ordinary skill have not been described in detail so as not to obscure claimed subject matter.

Unless specifically stated otherwise, it is appreciated that throughout this specification discussions utilizing terms such as "processing," "computing," "calculating," "determining," and "identifying" or the like refer to actions or processes of a computing device, such as one or more computers or a similar electronic computing device or devices, that manipulate or transform data represented as physical electronic or magnetic quantities within memories, registers, or other information storage devices, transmission devices, or display devices of the computing platform.

The system or systems discussed herein are not limited to any particular hardware architecture or configuration. A computing device can include any suitable arrangement of components that provides a result conditioned on one or more inputs. Suitable computing devices include multipurpose microprocessor-based computer systems accessing stored software that programs or configures the computing system from a general purpose computing apparatus to a specialized computing apparatus implementing one or more aspects of the present subject matter. Any suitable programming, scripting, or other type of language or combinations of languages may be used to implement the teachings contained herein in software to be used in programming or configuring a computing device.

Aspects of the methods disclosed herein may be performed in the operation of such computing devices. The order of the blocks presented in the examples above can be varied—for example, blocks can be re-ordered, combined, and/or broken into sub-blocks. Certain blocks or processes can be performed in parallel.

The use of "adapted to" or "configured to" herein is meant as open and inclusive language that does not foreclose devices adapted to or configured to perform additional tasks or steps. Additionally, the use of "based on" is meant to be open and inclusive, in that a process, step, calculation, or other action "based on" one or more recited conditions or values may, in practice, be based on additional conditions or values beyond those recited. Headings, lists, and numbering included herein are for ease of explanation only and are not meant to be limiting.

While the present subject matter has been described in detail with respect to specific aspects thereof, it will be appreciated that those skilled in the art, upon attaining an understanding of the foregoing, may readily produce alterations to, variations of, and equivalents to such aspects. Accordingly, it should be understood that the present disclosure has been presented for purposes of example rather than limitation, and does not preclude inclusion of such modifications, variations, and/or additions to the present subject matter as would be readily apparent to one of ordinary skill in the art.

What is claimed is:

1. A method comprising:
    receiving, by a central exchange component executed on a server system, a request to enable access to secured data, the request received from a first remote exchange component executed on a first computing system that is remote from the server system, the request including:
        encrypted identity data that is encrypted by the first remote exchange component via a first instance of an identity encryption module, and
        encrypted inquiry data that is encrypted by the first remote exchange component via a first instance of a first request encryption module;
    decrypting, at the central exchange component, the encrypted identity data via a second instance of the identity encryption module and the encrypted inquiry data via a second instance of the first request encryption module;
    receiving response data generated from a selected portion of the secured data, wherein the selected portion of the secured data is accessed based on the decrypted identity data and the decrypted inquiry data;
    encrypting, at the central exchange component, the response data via a first instance of a second request encryption module;
    re-encrypting, at the central exchange component, the decrypted identity data via the second instance of the identity encryption module; and
    providing, from the central exchange component and to a second remote exchange component executed on a second computing system remote that is remote from the server system and the first computing system, the encrypted response data and the re-encrypted identity data, wherein the second remote exchange component is configured to decrypt the encrypted response data via a second instance of the second request encryption module and further configured to decrypt the re-encrypted identity data via a third instance of the identity encryption module.

2. The method of claim 1, further comprising:
    providing, from the central exchange component and to the first remote exchange component, a verification token that is encrypted via the second instance of the first request encryption module;
    receiving, at the central exchange component and from the second remote exchange component, an encrypted token that includes the verification token that is encrypted via the second instance of the second request encryption module; and
    decrypting, at the central exchange component and via the second instance of the second request encryption module, the encrypted token,
    wherein accessing the secured data is responsive to receiving the encrypted token from the second remote exchange component.

3. The method of claim 1, further comprising:
generating, with the central exchange component, transformed data representing the selected portion of the secured data, wherein the transformed data is generated responsive to receiving the secured data via an input of the central exchange component,
wherein the response data includes the transformed data.

4. The method of claim 1, wherein (i) decrypting the identity data and (ii) re-encrypting the identity data, via the second instance of the identity encryption module, are each performed responsive to receiving, by the central exchange component, a data key.

5. The method of claim 4, wherein:
decrypting the inquiry data via the second instance of the first request encryption module is responsive to receiving, by the central exchange component, the data key, and
encrypting the inquiry data via the first instance of the second request encryption module is responsive to receiving, by the central exchange component, the data key.

6. The method of claim 1, further comprising:
encrypting, at the central exchange component and via an instance of an additional request encryption module, an additional request to enable access to additional secured data;
providing, from the central exchange component and to an additional remote exchange component of the server system, the encrypted additional request;
receiving, at the central exchange component and from the additional remote exchange component, encrypted additional response data generated from the additional secured data; and
decrypting, at the central exchange component and via the instance of the additional request encryption module, the encrypted additional response data,
wherein the selected portion of the secured data includes the decrypted additional response data.

7. A system comprising:
a server system comprising a memory component that is configured for storing a central exchange component, the server system communicatively coupled to a first computing system for executing a first remote exchange component and to a second computing system for executing a second remote exchange component, the central exchange component being capable of communicating with:
the first remote exchange component via a first secure channel on a computing network, and
the second remote exchange component via a second secure channel on the computing network,
wherein the server system is further configured for executing the central exchange component and thereby performing operations comprising:
receiving, from the first remote exchange component, a request to enable access to secured data, the request including:
encrypted identity data that is encrypted by the first remote exchange component via a first instance of an identity encryption module, and
encrypted inquiry data that is encrypted by the first remote exchange component via a first instance of a first request encryption module;
decrypting the encrypted identity data via a second instance of the identity encryption module and the encrypted inquiry data via a second instance of the first request encryption module;
receiving response data generated from a selected portion of the secured data, wherein the selected portion of the secured data is accessed based on the decrypted identity data and the decrypted inquiry data;
encrypting the response data via a first instance of a second request encryption module;
re-encrypting the decrypted identity data via the second instance of the identity encryption module; and
providing, from the central exchange component and to the second remote exchange component, the encrypted response data and the re-encrypted identity data, wherein the second remote exchange component is configured to (a) decrypt the encrypted response data via a second instance of the second request encryption module and (b) decrypt the re-encrypted identity data via a third instance of the identity encryption module.

8. The system of claim 7, wherein the server system is further configured for:
providing, from the central exchange component and to the first remote exchange component, a verification token that is encrypted via the second instance of the first request encryption module;
receiving, at the central exchange component and from the second remote exchange component, an encrypted token that includes the verification token that is encrypted via the second instance of the second request encryption module; and
decrypting, at the central exchange component and via the second instance of the second request encryption module, the encrypted token,
wherein accessing the secured data is responsive to receiving the encrypted token from the second remote exchange component.

9. The system of claim 7, wherein the server system is further configured for performing (i) said decrypting of the identity data and (ii) said re-encrypting of the identity data via the second instance of the identity encryption module responsive to receiving, by the central exchange component, a data key.

10. The system of claim 9, wherein the server system is further configured for
performing said decrypting of the inquiry data via the second instance of the first request encryption module responsive to receiving, by the central exchange component, the data key, and
performing said encrypting of the inquiry data via the first instance of the second request encryption module responsive to receiving, by the central exchange component, the data key.

11. The system of claim 7, wherein the server system is further configured for:
encrypting, at the central exchange component and via an instance of an additional request encryption module, an additional request to enable access to additional secured data;
providing, from the central exchange component and to an additional remote exchange component of the server system, the encrypted additional request;
receiving, at the central exchange component and from the additional remote exchange component, encrypted additional response data generated from the additional secured data; and
decrypting, at the central exchange component and via the instance of the additional request encryption module, the encrypted additional response data, wherein the selected portion of the secured data includes the decrypted additional response data.

\* \* \* \* \*